United States Patent [19]
Camerini-Otero et al.

[11] Patent Number: 5,460,941
[45] Date of Patent: Oct. 24, 1995

[54] METHOD OF TARGETING DNA

[75] Inventors: Rafael D. Camerini-Otero, Kensington; Margaret McIntosh, Chevy Chase; Carol S. Camerini-Otero, Kensington; Lance J. Ferrin, Rockville, all of Md.

[73] Assignee: The United States of America, as represented by the Secretary of the Department of Health and Human Services, Washington, D.C.

[21] Appl. No.: 89,910

[22] Filed: Jul. 12, 1993

Related U.S. Application Data

[63] Continuation of Ser. No. 733,744, Jul. 24, 1991, abandoned, which is a continuation-in-part of Ser. No. 611,268, Nov. 9, 1990, abandoned.

[51] Int. Cl.⁶ .......................... C12N 15/00; C12N 15/09
[52] U.S. Cl. .................... 435/6; 435/91.1; 435/91.53; 435/172.3; 935/16; 935/78
[58] Field of Search .......................... 435/6, 172.3, 196, 435/199, 69.1, 91.1, 41.53; 935/16, 78, 80

[56] References Cited

U.S. PATENT DOCUMENTS 4,888,274  12/1989  Radding et al. .......................... 435/6

OTHER PUBLICATIONS

Howard–Flanders et al, "Role of RecA protein spiral filaments in genetic recombination", Natrue 309: 215 (1984).
Moser et al, "Sequence–specific cleavage of double helical DNA by triple helix formation", Science 238: 645 (1987).
Hsieh et al, "Minimum homology required for stable joint molecule formation by recombinases", Keystone UCLA Meeting, Mar. 1989, p. 106.
Hsieh et al, "Recombinases can form DNA joint molecules in the absence of strand displacement", Cold Spring Harbor, Sep. 1988, p. 37.
Wells et al, "The chemistry and biology of unusual DNA structures adopted by oligopurione–oligopyrimidine sequences", FASEB Journal 2: 2939 (1988).
Camerini–Otero et al, "Right on target", The New Biologist 2: 337 (1990).
Reeck et al; Cell 50: 667 (1987).
Kowalczykowski et al; J. Mol. Biol. 193: 97 (1987).
Umlauf et al; J. Biol. Chem. 265: 16898 (1990).
Biochemistry, Second Edition, 1981, Stryer, W. H. Freeman and Company, San Francisco, pp. 754–756.
Hsieh et al; J. Biol. Chem. 264: 5089 (1989).
Maher et al; Science 245: 725 (1989).
Francois et al; Biochemistry 28: 9617 (1989).
Cooney et al; Science 241: 456 (1988).
Dreyer et al; Proc. Natl. Acad. Sci. USA 82: 968 (1985).
Rao, "A three–stranded DNA complex remains afer strand exchange mediated by rec A protein", in Molecular Mechanisms in DNA Replication, 1990, Alan R. Liss, Inc., pp. 387–398.
Register et al, "Electron microscopic visualization of the RecA protein–mediated pairing and branch migration phases of DNA strand exchange", J. Biol. Chem. 262: 12812 (1987).
Stasiak et al, "Visualization of RecA–DNA complexes involved in consecutive stages of an in vitro strand exchange reaction", Cold Spring Harbor Symposia on Quantitative Biology 49: 561 (1984).
Postel et al, "Evidence that a triplex–forming oligodeoxyribonucleotide binds to the c–myc promoter in HeLa cells, therby reducing c–myc mRNA levels", Proc. Natl. Acad. Sci. USA 88: 8227 (1991).

*Primary Examiner*—James Martinell
*Attorney, Agent, or Firm*—Knobbe, Martens, Olson & Bear

[57] ABSTRACT

The present invention relates to a method of forming a three-stranded DNA molecule wherein each strand of the three-stranded DNA molecule is hybridized (that is, non-covalently bound) to at least one other strand of the three-stranded DNA molecule. The method comprises:

contacting a recombination protein with a double-stranded DNA molecule and with a single-stranded DNA molecule sufficiently complementary to one strand of the double-stranded DNA molecule to hybridize therewith, which contacting is effected under conditions such that the single-stranded DNA molecule hybridizes to the double-stranded molecule so that the three stranded DNA molecule is formed.

18 Claims, 11 Drawing Sheets

FIG. 5A
```
56                              5'―――56―――→3'
76L   5' ACTGCGTAACGGTAGCATGA―――――――→3'
76R                             5'―――――ACCGATCTGACGTGAGTGAC 3'
96    5' ACTGCGTAACGGTAGCATGA―――――――ACCGATCTGACGTGAGTGAC 3'
```
FIG. 5B
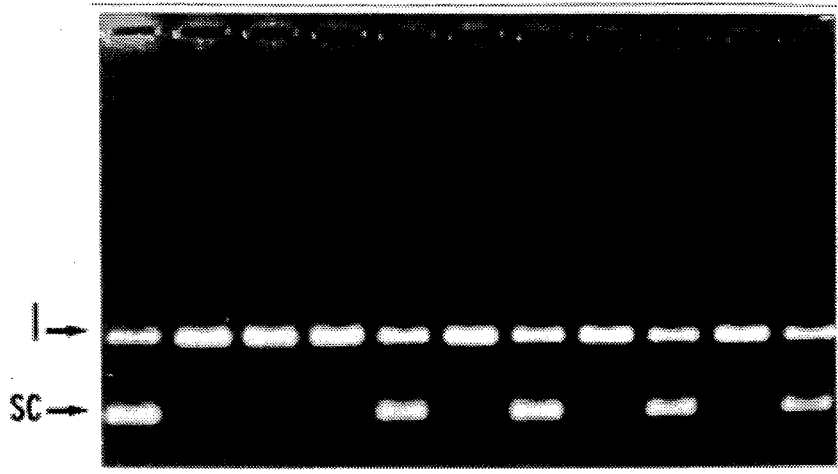
FIG. 5C
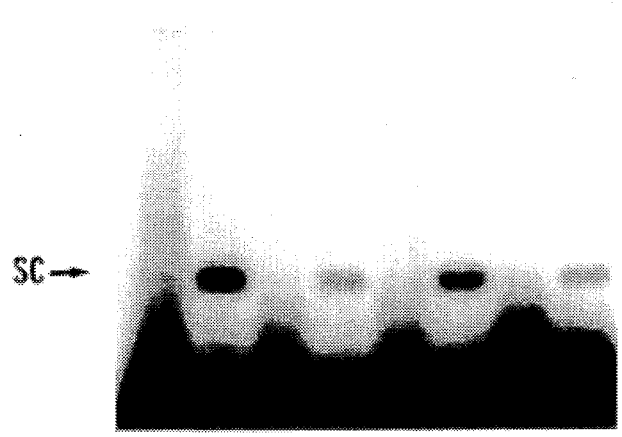

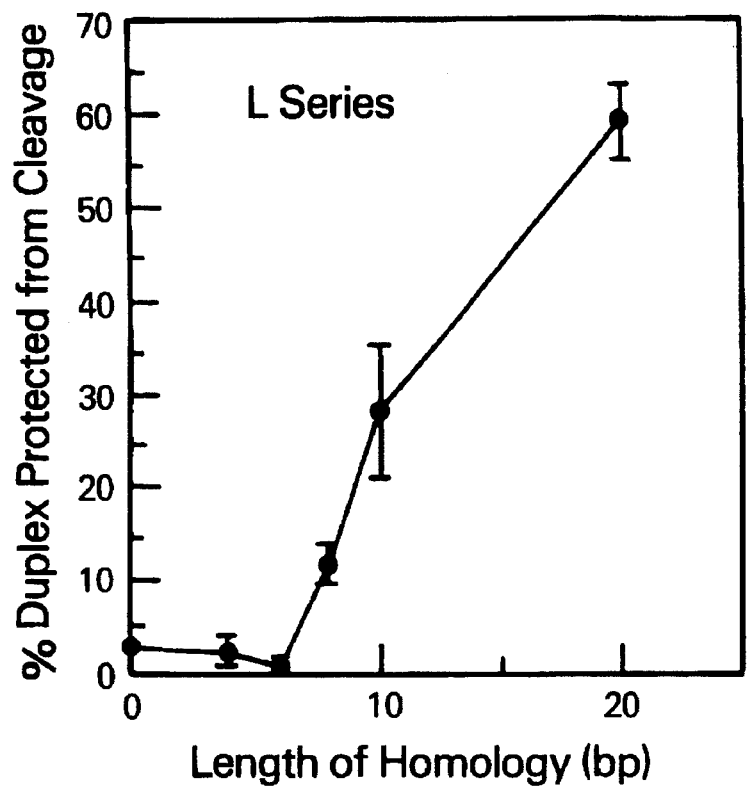
FIG. 7A
FIG. 7B
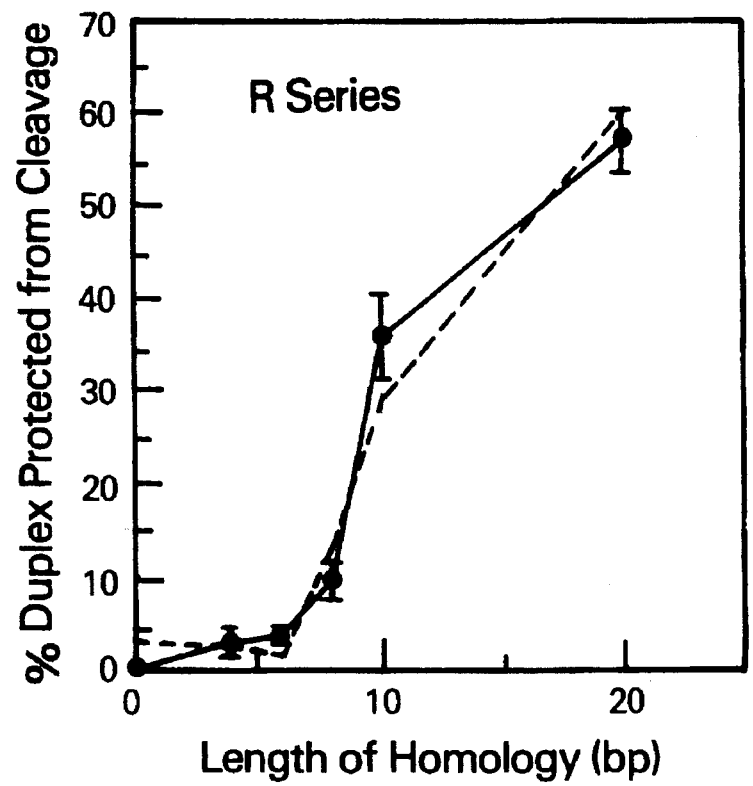

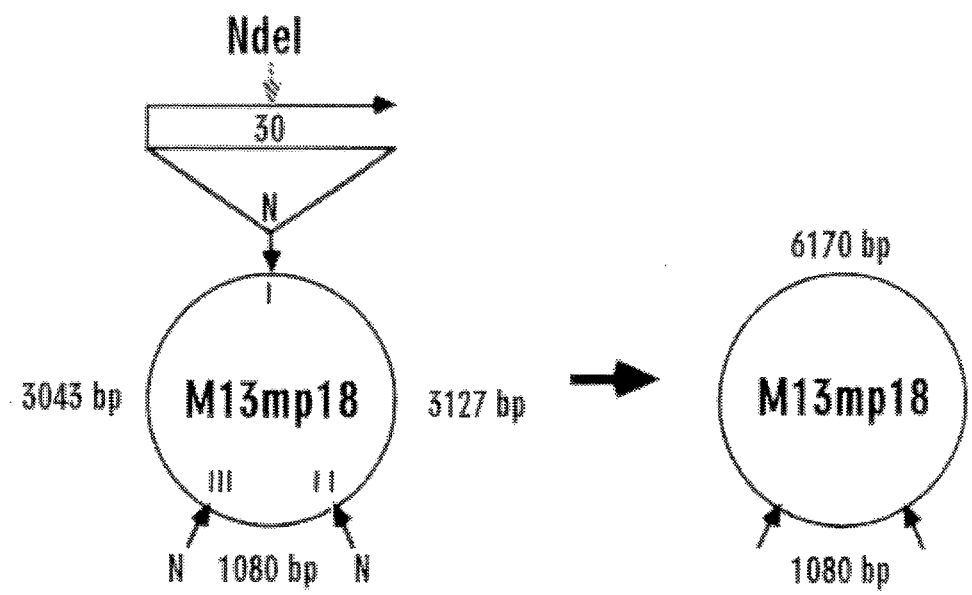
M13 mp18 has three cleavage sites for NdeI (N)
FIG. 8A
FIG. 8B
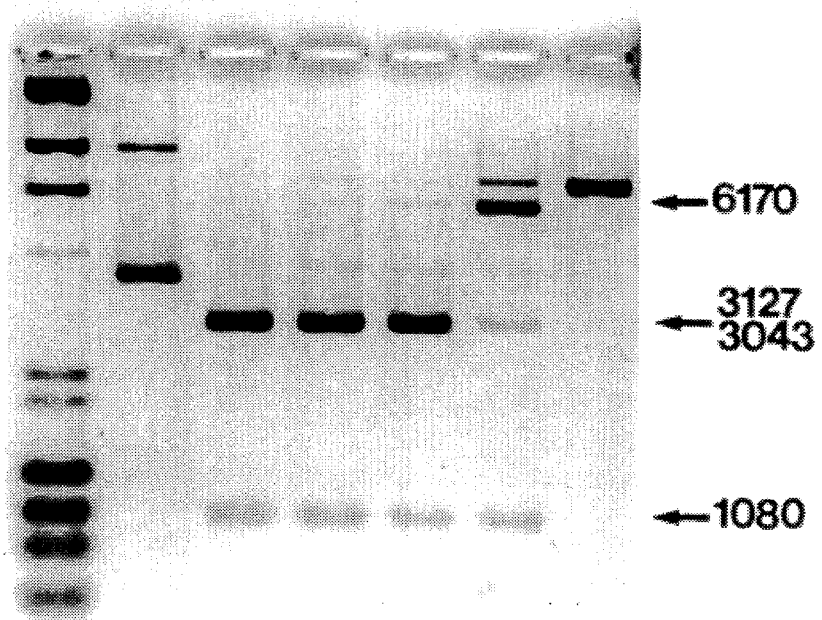

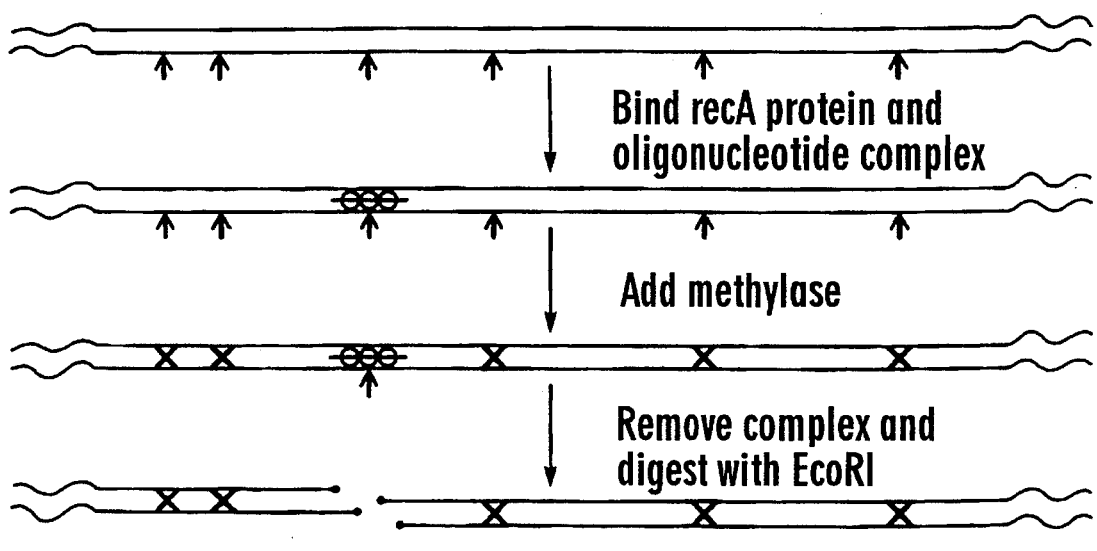

↑ EcoR I sites
↑ oligo overlap site

CF GENE

METHOD OF TARGETING DNA

This application is a continuation of application Ser. No. 07/733,744, filed Jul. 24, 1991, now abandoned, which is a continuation-in-part of application Ser. No. 07/611,088, filed Nov. 9, 1990, now abandoned.

BACKGROUND ON THE INVENTION

1. Technical Field

The present invention relates, in general, to a method of targeting DNA and, in particular, to a method of effecting sequence-specific targeting of DNA.

2. Background Information

Several groups have recently reported highly efficient cleavage of genomic DNA at specific sequences. For example, Szybalski and coworkers have cleaved *Saccharomyces cerevisiae* and *E. coli* genomes at a single introduced lac operator site (Koob et al, Science 250, 271 (1990)). These investigators first methylated Hae II sites in the DNA while using the lac repressor to protect the lac operator from methylation. After inactivation of the methylase and the repressor, the only Hae II site unmodified and available for cleavage was the lac operator site. The advantages of this approach were the high yield and high specificity. The disadvantage was that only a lac operator site could be cleaved.

A second approach was used by several investigators to cleave genomes as large as *S. cerevisiae*. This approach used the ability of synthetic homopyrimidine oligonucleotides to anneal to duplex homopyrimidine-homopurine tracts to form triple-helical structures. This approach was first used by Moser and Dervan (Science 238, 645 (1987)) to cleave a plasmid by equipping the oligonucleotide with an EDTA-Fe cleavage moiety. Subsequently, other cleavage moieties were attached to homopyrimidine oligonucleotides. For example, Schultz and coworkers attached staphylococcal nuclease (Pei et al, Proc. Natl. Acad. Sci. USA 87, 9858 (1990)), and Helene and coworkers attached a phenanthroline-copper derivative (Francois et al, Proc. Natl. Acad. Sci. USA 86, 9702 (1989)) as cleavage moieties. Dervan and coworkers have also used a guanine-rich cleavage oligonucleotide to form a triplex (Beal et al, Science 251, 1360 (1991)), and have cleaved DNA using a triplex and the methylation protection strategy described above (Strobel et al, Nature 350, 172 (1991)). The advantages of this targeting approach are efficiency and the ability to use oligonucleotides with a variety of derivatives. The disadvantage is that only homopyrimidine or guanine-rich oligonucleotides have been used successfully.

The practical use of previously reported strategies is severely limited because of the paucity, or indeed the complete absence, of possible cleavage sites in any particular DNA sequence. The present invention, on the other hand, provides a general method of cleaving DNA at any desired site, or pair of sites. Site-specific cleavage, however, is only a single embodiment of the present invention. In a broader sense, the invention relates to a method of targeting any desired sequence specifically and efficiently whether, it be for purposes of cleavage, protection or enrichment.

SUMMARY OF THE INVENTION

It is a general object of the invention to provide a rapid, efficient and general method of effecting sequence-specific targeting of DNA for purposes of, for example, cleavage, protection or enrichment.

The present invention relates to a method of forming a three-stranded DNA molecule wherein each strand of the three-stranded DNA molecule is hybridized (that is, non-covalently bound) to at least one other strand of the three-stranded DNA molecule. The method comprises:

contacting a recombination protein with a double-stranded DNA molecule and with a single-stranded DNA molecule sufficiently complementary to one strand of the double-stranded DNA molecule to hybridize therewith, which contacting is effected under conditions such that the single-stranded DNA molecule hybridizes to the double-stranded molecule so that the three stranded DNA molecule is formed.

Further objects, and advantages, will become clear from a reading of the disclosure that follows.

BRIEF DESCRIPTION OF THE DRAWINGS

FIG. 2. Synaptic complexes and joint molecules formed by recA.

FIG. 3. Formation of synaptic complexes with linear duplexes.

FIG. 5. The effect of directionality on synaptic complex and joint molecule formation. FIG. 5A. A 56-base oligonucleotide completely homologous to the polylinker region of pUC18 or having additional nonhomologous sequences at either or both the 5' and 3' ends. Sequence 76L (SEQ ID NO:23) has a nonhomologous region at the 5' end. Sequence 76R (SEQ ID NO:24) has a nonhomologous region at the 3' end. Sequence 96 (SEQ ID NO:25) has nonhomologous regions at both ends. FIG. 5B. Formation of synaptic complexes by recA can initiate at either the 5' or 3' end of the single-strand or at an internal site. Synaptic complex assays were carried out with $^{32}$P-labeled oligonucleotides. The band in lane 1 migrating just above linear pUC18 represents nicked duplex present in the starting substrate. FIG. 5C. Homology at the 5' end of the single-strand is preferred in joint molecule formation. Synaptic complex assays were deproteinized by the addition of SDS followed by electrophoresis and autoradiography. Lanes 1-8 correspond to lanes 4-11 in part B above. l, linear duplex; sc, supercoiled duplex.

FIG. 6. The minimal searching unit for homologous pairings.

FIG. 7. RecA pairs less than one helical repeat of the duplex DNA. FIG. 7A. Formation of synaptic complexes with the L series of oligonucleotides. Results represent the average of three independent observations. Percent protection of the duplex is normalized to a control reaction containing duplex DNA and recA. Error bars represent the standard error of the mean. FIG. 7B. Formation of synaptic complexes with the R series (solid line). Results represent the average of four independent observations. Shown for comparison is the corresponding data for the L series, dotted line. The detection and quantitation of small numbers of synaptic complexes was facilitated by the use of 200 ng of duplex DNA in these experiments.

FIG. 8. The specificity of the recA pairing reaction. FIG. 8A. A 30-base oligonucleotide homologous to M13mp18 spans one of three NdeI restriction endonuclease sites (N) in the duplex. The oligonucleotide sequence is 5'TATCAAC-CGGGGTACATATGATTGACATGC 3' (SEQ ID NO:1). The NdeI site is in bold. FIG. 8B. RecA targets synaptic complex formation to the homologous site in the duplex with high efficiency. The 30-base oligonucleotide was incubated with duplex DNA and recA in a synaptic complex assay followed by incubation with NdeI. Size markers (M) are lambda Hind III and phi X 174 Hae III fragments. Lane 6, M13mp18 duplex DNA digested with Bam HI yielding a full-length 7.2 kb linear fragment. For clarity, the ethidium-bromide stained gel is reproduced in reverse contrast.

FIG. 9. Schematic of the strategy used for sequence specific cleavage of DNA. This diagram shows cleavage at a single site.

FIG. 10.

FIG. 11.A. A schematic showing the positions of cleavage of the *E. coli* chromosome using two oligonucleotides homologous to sites in the uvrB and topA genes.

FIG. 12.

DETAILED DESCRIPTION OF THE INVENTION

Figure 1:
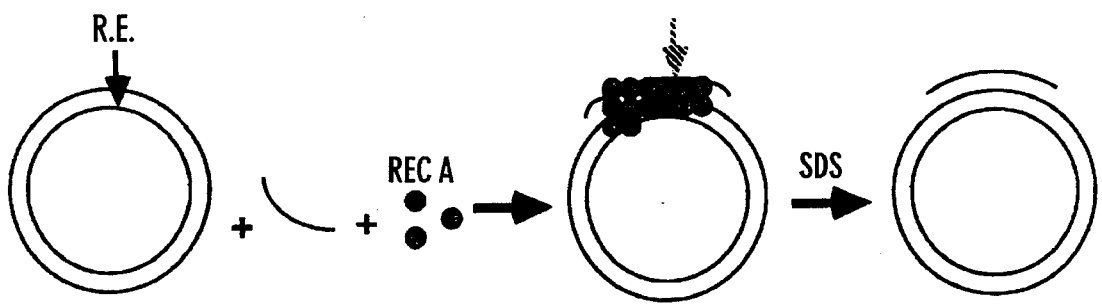
FIG. 1. Scheme for the formation of synaptic complexes and stable joint molecules. A duplex DNA and a homologous oligonucleotide are incubated in the presence of *E. coli* recA protein to form a synaptic complex in which the two DNAs are paired within a recA nucleoprotein filament. The formation of synaptic complexes is monitored by the inability of a restriction endonuclease to cleave the duplex within the region of pairing. If recA protein is removed from synaptic complexes by the addition of SDS detergent, stable, deproteinized joint molecules result.

The present invention relates to a method of effecting sequence-specific targeting of DNA. In general terms, the method utilizes the ability of a recombination protein, for example, the recA protein from E. coli, to pair an oligonucleotide to its homologous sequence in duplex DNA to form a three-stranded DNA molecule. A schematic of the formation of such a synaptic complex and stable joint molecule is given in FIG. 1.

The method to which the invention relates has wide applicability. It can be used to protect a specific sequence (that is, that sequence with which the oligonucleotide is complexed) from modification, for example, by a methylase, or, alternatively, from cleavage, for example, by a restriction enzyme. In addition, the present invention can also be used to effect site specific cleavage by attaching to the oligonucleotide a cleavage moiety, for example, a chemical cleavage moiety. Furthermore, the present method can also be used to accomplish site specific cleavage in a two-step process by, first, protecting the specific sequence from modification (by the formation of the three-stranded molecule) and, then, removing the oligonucleotide, thus making the prior-protected site available for cleavage (the other such sites being protected from cleavage by prior modification). In yet another embodiment, the present invention can be used to enrich a DNA pool for a desired sequence by derivatizing the oligonucleotide with one member of a binding pair, for example, biotin, and then selecting for the three-stranded molecule resulting from the complexation of the oligonucleotide with the desired duplex, using the other member of the binding pair, in this example, avidin. Purification of specific duplex DNA molecules can be accomplished in this manner. Other embodiments of the invention include the use of oligonucleotides linked to detectable labels for tagging specific duplex molecules, and the use of oligonucleotides bound to cross-linking reagents which, when activated, result in the formation of a stable three-stranded molecule. Other applications of the present method will be clear to one skilled in the art from a reading of this disclosure.

Oligonucleotides suitable for use in the invention can be designed so as to optimize desired results. For example, the length of the oligonucleotides can be adjusted for particular targeting protocols without undue experimentation.

While the present invention will be described in some detail with reference to the above-described protection and restriction/modification embodiments, one skilled in the art will appreciate the broader applicability of this methodology both to in vitro and in vivo systems.

The protection aspect of the invention is described in some detail in Example 7 below. As will be clear from a reading of that Example, recA can be used to afford protection, for example, from cleavage, of a particular site in a duplex DNA molecule by effecting the formation of a synaptic complex at that site. Formation of the complex between the oligonucleotide and the homologous duplex DNA is both rapid and efficient.

For purposes of clarity, the specific sequence of reactions involved in the restriction/modification embodiment of the invention is detailed in Examples 8–10 below. For target DNA that is not easily sheared, such as lambda DNA which is 48.5 kilobases (kb) long (Daniels et al in *Lambda II*, Hendrix et al, Eds. (Cold Spring Harbor, N.Y. 1983), pp. 519–676), the reactions are advantageously done in solution. Larger genomes, however, can be embedded in agarose microbeads. (See Examples 9 and 10.)

The first step in achieving sequence-specific cleavage of duplex DNA, in the exemplified restriction/modification embodiment, is the selection of the particular Eco RI site for cleavage. A homologous oligonucleotide, generally 30 to 60 bases long, is synthesized such that the Eco RI site is, advantageously, centered in the oligonucleotide. Oligonucleotides having the recognition sequence at the 5' or 3' end can also be used, however, reduced efficiency may be observed (see Example 9). The oligonucleotide and recA protein are incubated with duplex DNA and the complex formed at the site of homology. Eco RI methylase and S-adenosylmethionine are then added and allowed to methylate all available sites, but spare the site involved in the oligonucleotide and recA protein complex. The complex and methylase are then inactivated, and Eco RI restriction enzyme is added to cleave at the now uncovered Eco RI site.

Cutting at a single site is depicted in FIG. 9, however, two different oligonucleotides can be added at the same time. This allows isolation of a fragment from long or circular genomes. The following equation describes the yield of such a fragment:

$$\text{Yield } (\%) = (PC)^2 [1-(1-M)C]^X (1-N) \times 100$$

where

P is the efficiency of protection by recA protein of homologous sites from methylation (a value of 1 means complete protection), C is the efficiency of restriction enzyme cleavage, M is the efficiency of methylation of unprotected sites, X is the number of Eco RI sites found in the fragment, and N is the fraction of fragments destroyed by non-specific nucleases or shearing.

The three terms of the equation contain important parameters of the reaction. From the first terms, it is clear that protection of the homologous site should be maximized, and that drops in protection efficiency will be squared when two sites are involved. Protection efficiencies are assumed to be the same for both sites. Because of the second term, which is raised to the X power, the methylation should advantageously, be carried very close to completion, especially for long fragments with multiple internal Eco RI sites. From the third term, it is clear that nonspecific nucleases should be minimized, and, indeed, the use of proteins of high purity is preferred.

One skilled in the art will appreciate from a reading of the foregoing that while the oligonucleotides used can be underivatized, the versatility of targeting can be increased by derivatizing the oligonucleotide. Possible derivatives include proteins, biotin (as noted above), fluorescent dyes, chemically reactive moieties (for example, for cleavage) or photochemically reactive moieties. Derivatization can be effected using methods known in the art.

The method to which the invention relates has many applications, genomic mapping being one. The physical distance between two loci is simply the fragment size. Once a fragment is isolated, for example, using pulsed field gel electrophoresis, the complexity of finding a particular desired gene is reduced several orders of magnitude as compared to working with unfractionated genomic DNA.

One skilled in the art will appreciate from the foregoing that oligonucleotides can be designed to target any site of a DNA sequence, including sites within large genomes. Accordingly, oligonucleotides can be designed which can be used in an intracellular milieu to target cleavage, recombination or repression of specific genes.

Certain aspects of the invention are described in greater detail in the non-limiting Examples that follow.

EXAMPLES

Experimental details relating to Examples 1 to 7.
RecA protein:

Purified *E. coli* recA protein was provided by Dr. Stephen C. Kowalczykowski, Northwestern University Medical School.

DNA substrates:

pBR322 and pUC18 plasmid DNAs and M13mp18 replicative form DNA were from Pharmacia. Oligonucleotides were synthesized and purified by passage over a Mono Q column (Pharmacia) as described previously (Hsieh and Camerini-Otero, J. Biol. Chem. 264:5089 (1989)). Oligonucleotides were 5'-end labeled with $^{32}$P-gamma-ATP (New England Nuclear) and T4 polynucleotide kinase (Pharmacia) as described previously (Hsieh and Camerini-Otero, J. Biol. Chem. 264:5089 (1989)).

Figure 6A:
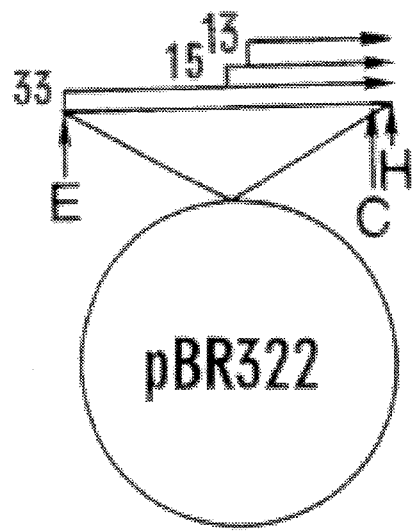
FIG. 6A. Oligonucleotides 33, 15 or 13 bases long are homologous to pBR322. Positions of Eco RI(E), Cla I (C) and Hind III (H) restriction endonuclease sites in the duplex are shown.

Oligonucleotides completely homologous to the plus strand of pBR322 (FIGS. 3 and 6) spanned pBR322 positions 15–29, 10–29 and 4359–29 for the 15, 20 and 33 base oligonucleotides, respectively (Sutcliffe, *Cold Spring Harbor Symp. Quant. Biol.* 49, 561 (1978)). The 20L series of oligonucleotides (FIG. 7) had varying amounts of homology to the plus strand of pBR322 at the 3' end and spanned positions 10–29, 20–29, 22–29, 24–29, and 26–29 for 20, 10, 8, 6, and 4 bases, respectively. The 20R series (FIG. 7) had homology to the plus strand of pBR322 at the 5' end and spanned positions 20–39, 20–29, 20–27, 20–25, and 20–23 for 20, 10, 8, 6 and 4 bases, respectively. Oligonucleotides homologous to the plus strand of pUC18 (FIG. 2) spanned positions 230–285, 230–267, 230–255, and 230–249 for the 56, 38, 26 and 20 base oligonucleotides, respectively (Norrander et al, *Gene* 26, 101 (1983)). The 33-base oligonucleotide homologous to positions 4359–29 of pBR322 was not paired to the polylinker region of pUC18. The 20 base oligonucleotide used in the experiment shown in FIG. 4 was homologous to positions 248–267 of the negative strand of pUC18. The oligonucleotides shown in FIG. 5 contained 56 bases homologous to the plus strand of pUC18 corresponding to positions 230–285. The 30 base oligonucleotide homologous to the plus strand of M13mp18 (FIG. 8) spanned positions 6831–6860 (Yannisch-Perron et al, *Gene* 33, 103 (1985)). DNA concentrations are expressed as moles of nucleotide or by weight.

Synaptic complex formation:

Synaptic complexes were formed by incubating 1.8 µM (15 ng) oligonucleotide, 18 µM duplex DNA (150 ng) and 1.5 µM (1.5 µg) recA protein in a buffer containing 20 mM Tris-HCl, pH 7.5, 0.4 mM dithiothreitol, 12.5 mM $MgCl_2$, 0.3 mM ATP-gamma-S (Fluka) and 1.1 mM ADP (Sigma) in a total volume of 25 µl for 15 min at 37° C. Following synaptic complex formation, 10–20 units of the appropriate restriction endonuclease (New England Biolabs) were added and incubation continued for an additional 5 min. The reaction was quenched by the addition of SDS and EDTA to a final concentration of 1% and 10 mM, respectively. Reactions were electrophoresed on 1% agarose gels in 40 mM Tris-acetate, pH 8.0, 1 mM EDTA and 1 µg/ml ethidium bromide at 0.6 V/cm for 14–16 h at room temperature. Quantitation was determined by comparison of reacted assays with 150 ng of unreacted duplex DNA using densitometer scanning of Polaroid 665 negatives. Recoveries of intact duplex DNA in synaptic complex assays were compared to a standard containing 150 ng unreacted duplex DNA. In some cases, synaptic complex assays were quenched by the addition of 1% SDS and electrophoresed on 1% agarose gels in 89 mM Tris-borate, pH 8.3, 5 mM $MgCl_2$ at 0.6 V/cm for 14–16 h at room temperature.

Deproteinized joint molecules:

Synaptic complexes were formed as described above except that 5'-$^{32}$P-labeled oligonucleotides were used. The reactions were quenched by the addition of SDS and EDTA and electrophoresed as described. The gels were then fixed and exposed on Kodak XAR-2 film. In some cases, joint molecules were deproteinized by proteinase K (Boehringer Mannheim) treatment and phenol:chloroform extraction as described previously prior to electrophoresis (Hsieh et al, *Genes Devel.* 4, 1951 (1990)). Quantitation of joint molecules was determined by a reconstruction experiment in which a $^{32}$P-labeled 56-base oligonucleotide was annealed to known quantities of M13mp19 single-strand DNA at 65°

C. or in the presence of recA. (No difference was observed in the efficiency of annealing.) Following electrophoresis and autoradiography, the relative intensities of these annealed standards were compared with those of joint molecules.

EXAMPLE 1

Formation of Synaptic Complexes and Joint Molecules

The experimental scheme for the formation of synaptic complexes and stable joint molecules by recA is shown in FIG. 1. Formation of synaptic complexes is accomplished by incubating a duplex DNA such as a supercoiled plasmid DNA, a homologous oligonucleotide and recA protein. The oligonucleotide spans a restriction endonuclease recognition site in the duplex DNA. Formation of a synaptic complex involving recA protein, oligonucleotide and the duplex DNA renders the duplex resistant to cleavage by the restriction endonuclease. The restriction endonuclease footprint corresponding to a synaptic complex can be visualized on ethidium bromide-stained agarose gels as supercoiled plasmid DNA remaining after incubation of complexes with the appropriate restriction endonuclease. RecA protein can be dissociated from these synaptic complexes by adding EDTA and SDS detergent, and deproteinized joint molecules result in which the oligonucleotide (5' end-labeled with $^{32}$P) is stably paired with the duplex. The presence of joint molecules can be determined by assaying for the appearance of $^{32}$P label migrating on agarose gels at the position of duplex DNA.

The formation of joint molecules by recA in the presence of ATP and an ATP regenerating system was examined. It had previously been observed that, under these reaction conditions, stable, deproteinized joint molecules were formed by recA between a linear duplex and a single-strand circular DNA sharing less than 60 bp of homology (Hsieh et al, *Genes Devel.* 4, 1951 (1990)). Stable, deproteinized joint molecules were formed by recA between pUC18 supercoiled DNA and a homologous 56-base oligonucleotide. In the presence of ATP hydrolysis, deproteinized joint molecules were recovered after 1 min but were very unstable; after 3 min, half of the joint molecules had dissociated, and after a 15 min incubation, no deproteinized joint molecules were recovered. Once the initial round of pairing and dissociation had occurred, it appeared that the duplex was unable to participate in additional rounds of pairing. Due to the transient nature of this pairing, footprinting of synaptic complexes was not possible in the presence of ATP. It was observed that replacement of ATP with a nonhydrolyzable analogue of ATP, ATP-gamma-S, and ADP allowed freezing of the pairing reaction and accumulation of intermediates.

Figure 2A:
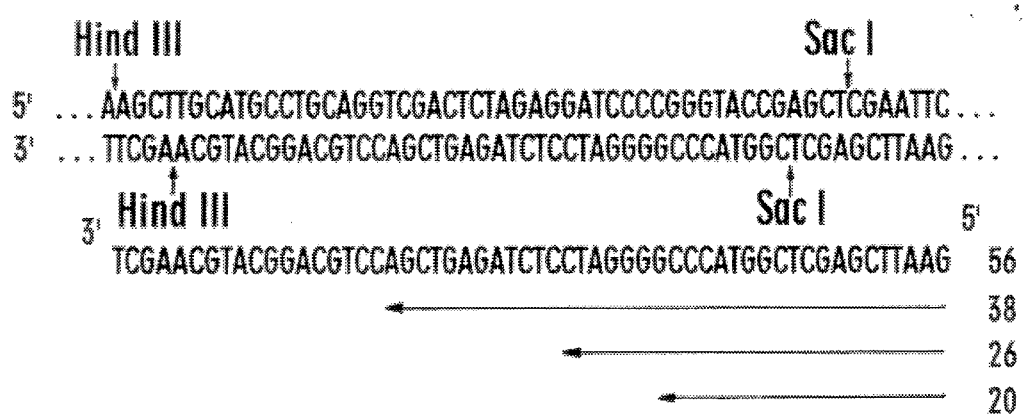
FIG. 2A. Oligonucleotides having 56 (SEQ ID NO:19), 38, 26 or 20 bases of homology to pUC18 duplex DNA (SEQ ID NO:20) that span a Sac I site.

The formation of synaptic complexes and stable joint molecules by recA protein in the presence of 0.3 mM ATP-gamma-S and 1.1 mM ADP is shown in FIG. 2. $^{32}$P-labeled oligonucleotides homologous to pUC18 plasmid polylinker sequences were incubated with supercoiled pUC18 plasmid DNA in the presence of recA protein followed by the addition of Sac I restriction endonuclease. As depicted in FIG. 2A, all the oligonucleotides spanned a unique Sac I restriction endonuclease recognition site in the pUC18 plasmid.

Figure 2B:
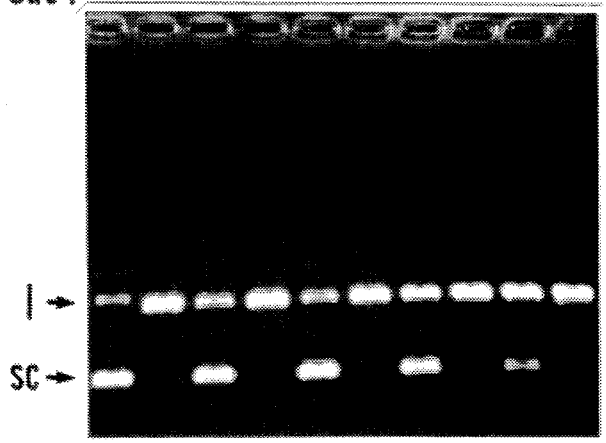
FIG. 2B. Synaptic complexes formed by recA. $^{32}$P-labeled oligonucleotides, pUC 18 supercoiled plasmid DNA and recA protein were co-incubated. Following incubation with the appropriate restriction endonuclease, the reactions were brought to 1% SDS and electrophoresed on a 1% agarose gel containing ethidium bromide. The footprint of synaptic complexes is represented by the presence of supercoiled plasmid DNA remaining after incubation with a restriction endonuclease.

Synaptic complexes were formed with 20 bases of homology shared between the oligonucleotide and the duplex DNA (see FIG. 2B, lane 9). Quantitation of the amount of supercoiled DNA protected from digestion by Sac I indicated that 70–75% of the duplex DNA was present as synaptic complexes when the oligonucleotide contained 56 or 38 bases of homology (lanes 3 and 5). Fifty-five percent and 20% of the duplex were converted to synaptic complexes with 26 and 20 bases, respectively, of homology. Formation of synaptic complexes required the presence of both recA protein and the homologous oligonucleotide. A control in lane 1 indicates that when the duplex was incubated with oligonucleotide and recA, but without restriction enzyme, the supercoiled DNA remained intact. As shown in lane 10, the footprint of the synaptic complex did not extend appreciably beyond the region of the duplex that is colinear with the oligonucleotide since synaptic complexes do not afford protection from cleavage by Hind III which cleaves at a site located 14 bp from the region spanned by the 38-base oligonucleotide. In addition, in this assay, a nonhomologous oligonucleotide does not result in the formation of a synaptic complex by recA.

Figure 2C:
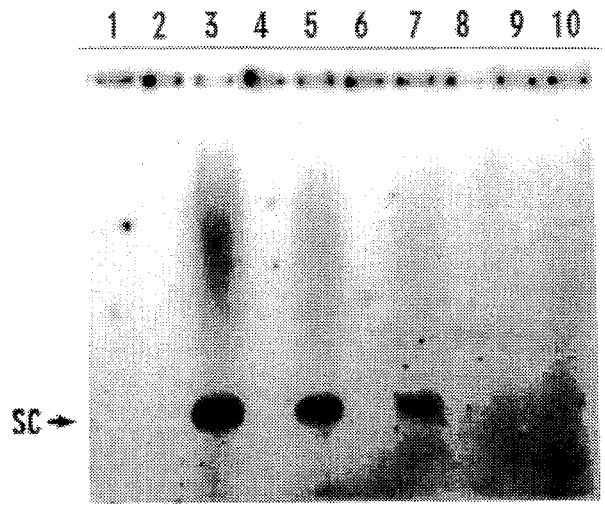
FIG. 2C. Joint molecules formed by recA. An autoradiogram of the same agarose gel demonstrates the formation of joint molecules as indicated by the presence of $^{32}$P-label migrating at the position of supercoiled plasmid DNA. 1, linear duplex; sc, supercoiled duplex.

RecA can form joint molecules that are stable when deproteinized between a homologous $^{32}$P-labeled oligonucleotide and pUC18 plasmid DNA (FIG. 2C). As few as 26 bases of homology shared between the oligonucleotide and the duplex DNA is sufficient for the formation of joint molecules in this assay whereas twenty bases of homology is not sufficient. Quantitation of the recovery of stable joint molecules indicates that approximately 20–50% of the pUC18 duplex was paired with a homologous oligonucleotide 56 bases long when the complexes were electrophoresed in TAE buffer (see description of FIG. 2). As was observed for synaptic complexes, the efficiency of joint molecule formation by recA increases as a function of the length of homology available for pairing. These deproteinized joint molecules dissociate when the superhelical strain is relieved upon linearization at a restriction endonuclease site located outside the region of pairing (FIG. 2C, lane 10).

The joint molecules formed between a duplex DNA and an oligonucleotide are not stabilized by residual recA protein. When synaptic complexes were deproteinized by treatment with SDS, proteinase K and phenol/chloroform extraction, the number of stable joint molecules recovered was unchanged.

The assay conditions used for the formation of synaptic complexes were those that proved optimal for joint molecule formation with 56 bp of homology. The formation of joint molecules exhibited a sharp optimum for an oligonucleotide concentration of 1.2 µM, with 0.9 µM oligonucleotide yielding no joint molecules; increasing the oligonucleotide concentration to 1.8 µM resulted in no further increase in the yield of joint molecules. The amount of recA used in these assays (1.5 µM) is saturating with respect to the single-strand oligonucleotide concentration. The ready detection of synaptic complexes and joint molecules was dependent on the presence of both ATP-gamma-S and ADP in a 1:3 molar ratio. Alteration of the ratio of ATP-gamma-S to ADP or the concentration of these two cofactors reduced the efficiency of both synaptic complex and joint molecule formation.

It is well established that divalent cations are essential for recA activity in vitro. A study was undertaken to determined whether $Mg^{2+}$ is required to stabilize joint molecules. Synaptic complexes were formed in the presence of recA as described in FIG. 2. The reactions were deproteinized by the addition of SDS alone and the reaction products analyzed by electrophoresis on agarose gels containing 5 mM $MgCl_2$. Although the recovery of joint molecules in the presence of $Mg^{2+}$ was 2–4 fold higher than when $Mg^{2+}$ was omitted from the electrophoresis step, no qualitative differences were observed, i.e., stable joint molecules were formed with oligonucleotides containing 26 bases but not 20 bases of homology.

The data presented in FIG. 2 indicate that the formation of synaptic complexes in the presence of ATP-gamma-S is an intermediate step in the pathway leading to the formation of stable, deproteinized joint molecules. The formation of deproteinized joint molecules and synaptic complexes containing recA exhibit a dependence on the length of homology available for painting. Also, the formation of both synaptic complexes and joint molecules occurs with relatively high efficiency for 56 bases of homology; that is, upon deproteinization of these synaptic complexes, most of the duplex DNA is still paired with the oligonucleotide in stable joint molecules in the presence of $Mg^{2+}$.

EXAMPLE 2

Synaptic Complexes Containing Linear Duplex DNA

Figure 3A:
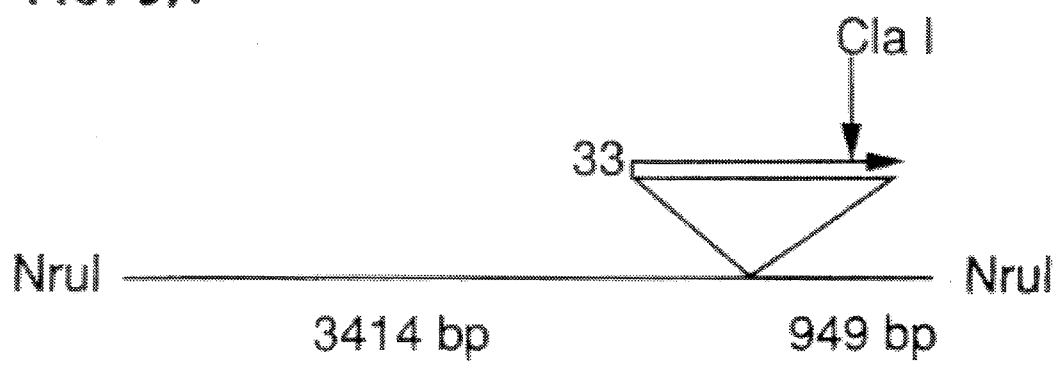
FIG. 3A. Map of the DNA substrates showing the 33-base oligonucleotide homologous to the linear pBR322 duplex and the location of the Cla I site.
Figure 3B:
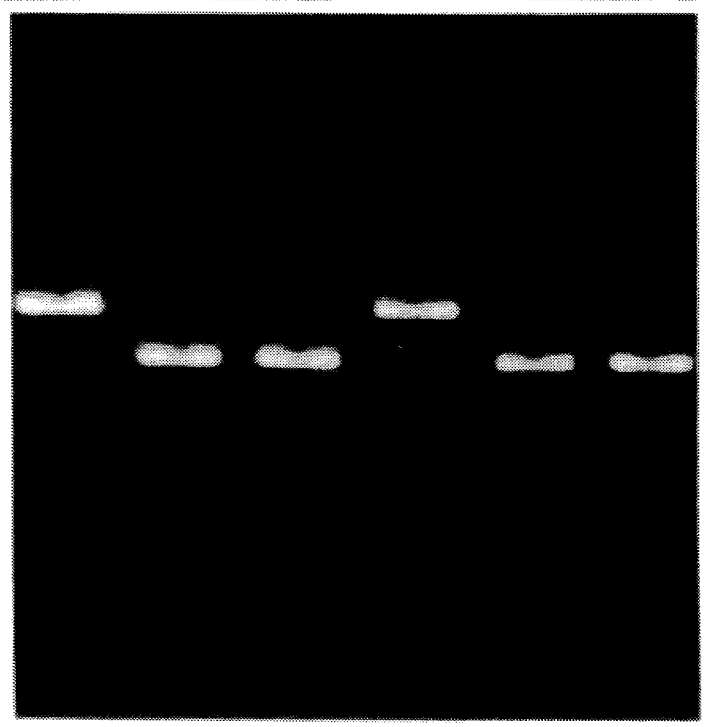
FIG. 3B. Synaptic complex assay with a linear duplex. The nonhomologous oligonucleotide is an M13mp18 sequence corresponding to positions 6228–6260. H, homologous 33-base oligonucleotide; NH, nonhomologous 33-base oligonucleotide.

Superhelical strain is not essential for the formation of synaptic complexes involving very short regions of homology. The formation of synaptic complexes involves recA, a linear duplex and a homologous oligonucleotide 33 bases long (FIG. 3A). In FIG. 3B, it is readily seen that recA formed synaptic complexes between these two substrates resulting in protection of the linear duplex from cleavage by Cla I (lane 4). In the absence of either recA or oligonucleotide (lanes 2 and 6, respectively) or in the presence of a nonhomologous oligonucleotide (lane 5), synaptic complexes were not formed.

EXAMPLE 3

Footprinting Synaptic Complexes

Figure 4:
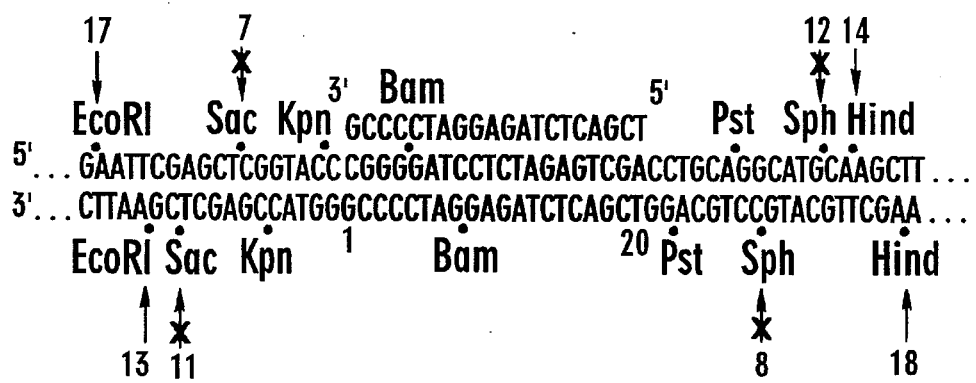
FIG. 4. Extent of the restriction endonuclease footprint of synaptic complexes. Synaptic complexes were formed with a homologous 20-base oligonucleotide (SEQ ID NO:21) and pUC18 duplex DNA (SEQ ID NO:22) in the presence of recA. The complexes were incubated with a variety of restriction endonucleases whose cleavage sites are indicated by the arrows. Protection from cleavage afforded by the synaptic complex extended to Sac I and Sph I sites. No protection was observed at Eco RI or Hind III sites. Numbers indicate the length from the end of the oligonucleotide to the proximal cleavage site.

The extent of protection from restriction endonuclease cleavage conferred by a recA synaptic complex was mapped (FIG. 4). A 20-base oligonucleotide homologous to a region in the polylinker sequence of pUC18 plasmid DNA was incubated in the presence of supercoiled pUC18 and recA to allow the formation of synaptic complexes. Protection was seen at sites for Bam HI, Kpn I, Pst I, Sac I and Sph I restriction endonucleases. However, cleavage by Eco RI and Hind III was unimpaired by the presence of the synaptic complex. Accordingly, the footprint of the synaptic complex apparently extends approximately 13–14 bases beyond the 5' and 3' ends of the paired oligonucleotide and is symmetrical.

EXAMPLE 4

Directionality of Synaptic Complex and Joint Molecule Formation

The apparent directionality of joint molecule formation is influenced by the choice of DNA substrates, the length of shared homology and the relative stabilities of joint molecules formed with opposite polarities (Konforti et al, *J. Biol. Chem.* 265, 6916 (1990); Rao et al, *Proc. Natl. Acad. Sci.* 88, 2984 (1991)). Therefore, the directionality of both synaptic complex formation and joint molecule formation involving a supercoiled duplex and an oligonucleotide was examined. The formation of synaptic complexes involving 56 bp of homology does not exhibit directionality. Synaptic complexes were formed by recA regardless of the positioning of the homologous sequence with respect to the ends of the oligonucleotide. In the experiment in FIG. 5, a 56-base oligonucleotide homologous to the polylinker region of pUC18 was used or one of several other oligonucleotides having the same 56-base sequence plus 20 bases of nonhomologous sequence at the 5' end, at the 3' end or at both the 5' and 3' ends of the oligonucleotide (FIG. 5A). In all cases, synaptic complexes were formed with about equal efficiencies (FIG. 5B, lanes 5, 7, 9, 11). In contrast, formation of stable joint molecules by recA exhibited polarity showing a strong preference for homology at the 5' end of the oligonucleotide; the number of joint molecules formed with the 76R oligonucleotide was half as many as with the 56-base oligonucleotide (FIG. 5C, lanes 2 and 6) whereas the 76L oligonucleotide (lane 4) or 9,6 oligonucleotide (lane 8) yielded ten-fold fewer joint molecules.

EXAMPLE 5

Minimum Structure Required for the Homology Search

Figure 6B:
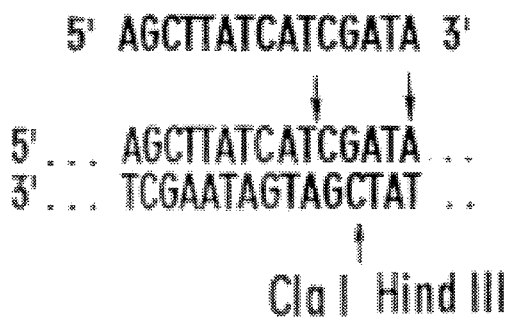
FIG. 6B. Nucleotide sequence of the 15-base oligonucleotide (SEQ ID NO:26) and corresponding duplex sequence (SEQ ID NO:27) showing positions of Cla I and Hind III cleavage. Bases in the duplex that comprise all or part of the recognition sequence for Cla I and Hind III are indicated in bold.
Figure 6C:
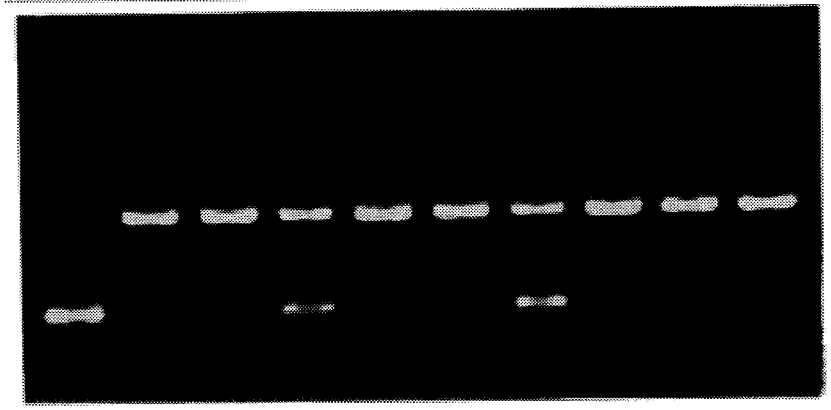
FIG. 6C. Formation of synaptic complexes with an oligonucleotide 15 bases long. Synaptic complexes were formed with the 15-base oligonucleotide as described above. Lanes 2-4, incubation with Hind III; lanes 5-7, incubation with Cla I; lanes 8-10, incubation with Eco RI.

Three oligonucleotides, 33, 15 or 13 bases long and homologous to a pBR322 sequence (FIG. 6A) were incubated with pBR322 supercoiled plasmid DNA in the presence of recA. Potential cleavage sites for the 15 base oligomer are shown in FIG. 6B and the footprint is shown in FIG. 6C. The 15 base oligomer was of sufficient length to form synaptic complexes as evidenced by resistance to cleavage by Hind III and Cla I endonucleases (lanes 4 and 7). In this assay, use of a 33-base oligomer resulted in the formation of synaptic complexes, but a 13-base oligomer did not. Control experiments indicate that the formation of synaptic complexes required the presence of both oligonucleotide and recA. The footprint of the synaptic complex did not extend appreciably beyond the region of pairing (see FIG. 6C, lane 10). This experiment also demonstrates that formation of synaptic complexes by recA was not restricted to any particular sequence since recA paired homologous DNAs containing either a pUC18 (FIG. 2) or a pBR322 sequence (FIG. 3).

EXAMPLE 6

Nucleation of Pairing Involves One-Half of a Helical Turn of the Nucleoprotein Filament To determine the minimum homology recognized by recA in a synaptic complex, a series of oligonucleotides 20 bases long was used that contained varying amounts of homology at the 5' or 3' end to a region of pBR322 flanking a Cla I site (see Table I). This experiment not only establishes the minimum homology recognized by recA in this assay, but also definitively establishes whether the initiation of pairing by recA exhibits directionality. The results shown in FIG. 7 indicate that recA can pair as few as 8 bases of homology at either the 5' or 23' end albeit at low efficiency (10% and 12% respectively). These results establish that the thresholds for nucleoprotein filament formation and homologous pairing are different and that either the 5' or 3' end of a single-strand DNA can nucleate pairing. Fifteen bases are required to form the structure that can carry out the homology search, but only one-half of the bases in this structure need be recognized and paired by recA.

TABLE 1

SEQUENCES OF OLIGONUCLEOTIDES CONTAINING DECREASING AMOUNTS OF HOMOLOGY TO pBR322

| | Sequence | Homology (bases) |
|---|---|---|
| 20L Series | | |
| SEQ. ID NO. 7 | 5' TTGACAGCTTATCATCGATA 3' | 20 |
| SEQ. ID NO. 8 | GAATATATGCATCATCGATA | 10 |
| SEQ. ID NO. 9 | GAATATATGCCACATCGATA | 8 |
| SEQ. ID NO. 10 | GAATATATGCCATGTCGATA | 6 |
| SEQ. ID NO. 11 | GAATATATGCCATGGAGATA | 4 |
| SEQ. ID NO. 12 | GAATATATGCCATGGATCGT | 0 |
| 20R Series | | |
| SEQ. ID NO. 13 | ATCATCGATAAGCTTTAATG | 20 |
| SEQ. ID NO. 14 | ATCATCGATAGAATATATGC | 10 |
| SEQ. ID NO. 15 | ATCATCGAGCGAATATATGC | 8 |
| SEQ. ID NO. 16 | ATCATCTCGCGAATATATGC | 6 |
| SEQ. ID NO. 17 | ATCAGATCGCGAATATATGC | 4 |
| SEQ. ID NO. 18 | CGACGATCGCGAATATATGC | 0 |

Sequences in bold correspond to the bases homologous to pBR322.
Underlined sequences correspond to the position of the Cla I restriction site on the duplex.

EXAMPLE 7

Targeting of an Oligonucleotide by recA

A study was undertaken to determine to what extent recA can discriminate among several similar but distinct target sequences that reside within a single duplex molecule. Supercoiled M13mp18 replicative form DNA which has three Nde I recognition sites was incubated in the presence of recA with a 30-base oligonucleotide containing the Nde I recognition sequence as well as adjacent sequence from one of the three Nde I sites in M13mp18 (site I, see FIG. 8A). The formation of a synaptic complex exclusively at site I was monitored by the appearance of a 6170 bp M13mp18 fragment following digestion of synaptic complexes with Nde I endonuclease. Such a fragment can only come about by cleavage at both sites II and III without cleavage at site I.

RecA was able to target pairing exclusively to site I in the majority of the DNA molecules (FIG. 8B, lane 5). Such targeting required the presence of both oligonucleotide and recA (lanes 3 and 4). The presence of a 1080 bp fragment in all samples incubated with Nde I is a control for the extent of Nde I cleavage at both unprotected sites II and III. Quantitation of the amounts of each species in lane 5 indicates that the level of discrimination of recA for pairing at the target site I over sites II and III is about 7–8 fold under these conditions.

Experimental details relating to Examples 8–10.
Oligonucleotides:

Oligonucleotides were purified on an FPLC Mono Q column (Pharmacia) using a NaCl gradient from 100 mM to 1M in 20 mM NaOH. Aliquots of peak fractions were labeled with $^{32}$P and run on polyacrylamide gels. The purest fractions were pooled, ethanol precipitated, and dissolved in water. Concentrations were determined by assuming that 1 OD unit at 260 nM is 33 µg.

RecA:

RecA protein was purified using a strain and a detailed protocol generously provided by Stephen Kowalczykowski of the Northwestern University Medical School in Chicago. The strain used was JC12772 (Uhlin et al., *J. Bacteriol.* 148, 386 (1981)). The purification was based on the spermidine precipitation method (J. Griffith et al, *Biochemistry* 24, 158 (1985)), and employed a single-stranded DNA agarose column with ATP elution (Cox et al *J. Biol. Chem.* 256, 4676 (1981)) and a Mono Q column to greatly reduce trace nuclease contamination. Removal of such contamination is important in order to avoid undesirable non-specific nicking of the DNA. The concentration of recA protein was measured using the extinction coefficient of [1]

$E_{280}=5.9$ (Craig et al, *J Biol . Chem.* 256, 8039 (1981)).

EXAMPLE 8

Sequence Specific Cleavage of Lambda DNA

Figure 10A:
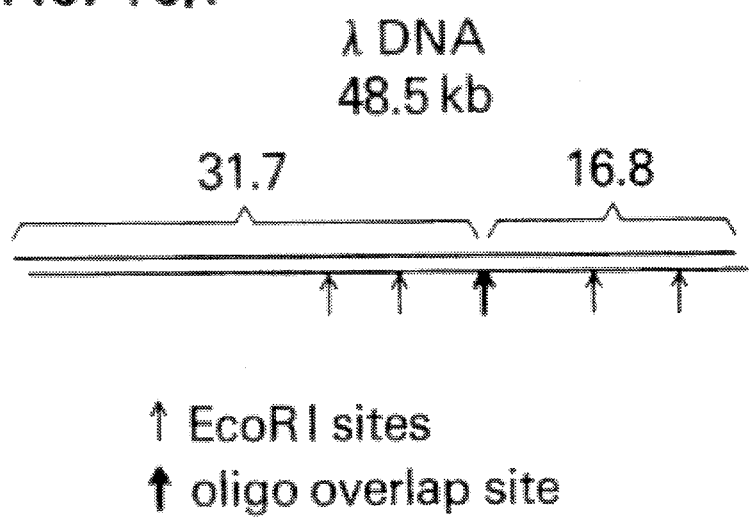
FIG. 10A. A schematic showing the position of cleavage of lambda DNA using an oligonucleotide homologous to the site shown by the bold arrow. Lambda DNA contains 5 Eco RI sites, including the one shown by the bold arrow.
Figure 10B:
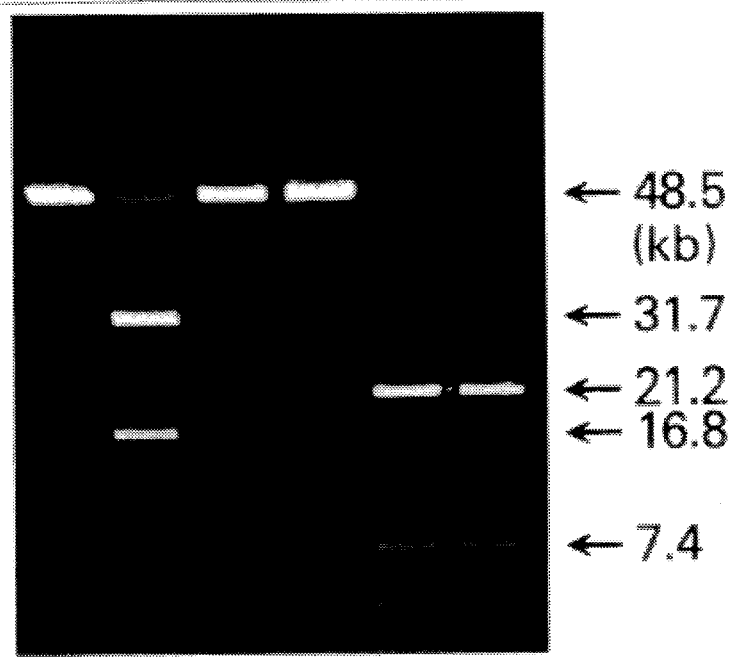
FIG. 10B. Agarose gel stained with ethidium bromide showing sequence-specific cleavage of lambda DNA. Lane 2 shows the complete cleavage reaction and the other lanes had components omitted as shown. Unmethylated lambda DNA was first protected by incubating with recA protein and an oligonucleotide 30 bases long identical to the lambda sequence from position 31,734 to 31,763. The sequence was 5'-TCACGCCGGAAGTGAATTCAAACAGGGTTC-3' (SEQ. ID NO: 2). After 10 minutes at 37° C. a minimal volume of Eco RI methylase and S-adenosylmethionine was added and the reaction was allowed to proceed for 20 minutes. The recA protein and methylase were then inactivated by heating for 15 minutes at 65° C. Eco RI restriction enzyme was added to the tube at 37° C., and the reaction was allowed to proceed for 60 minutes. The reaction volume was 40 µl and contained, in order of addition: 25 mM Tris-acetate (pH 7.5), 4 mM Mg-acetate, 0.4 mM dithiothreitol, 0.5 mM spermidine, 10 µg of recA protein, 100 µM EGTA, 1.1 mM ADP, 0.3 mM ATP-gamma-S (Fluka BioChemica), 0.18 µg of oligonucleotide, 0.9 µg of lambda DNA, 4 µg of acetylated bovine serum albumin (BSA), 3.8 units of Eco RI methylase, 120 µM S-adenosylmethionine, and 20 units of Eco RI restriction enzyme (all reagents listed from lambda DNA on were from New England Biolabs). The Tris-acetate, dithiothreitol, spermidine, and buffers used in the final recA protein purification steps were passed through Chelex 100 (Bio-Rad) columns to remove trace metal contaminants. The reactions were stopped with 5 µl of 6% sodium dodecyl sulfate (SDS), 90 mM EDTA and 0.1% bromophenol blue. 20 µl of the final reaction mixtures were mixed with 60 µl of 0.5% InCert agarose at 65° C. and allowed to set in the wells of a 1.5% agarose gel. The gel was run by pulsed field electrophoresis on a CHIEF-DRII system (Bio-Rad) for 36 hours at 12° C., 180 V, and 2.5 s switch time.

A demonstration of the sequence-specific cleavage of lambda DNA at a single site is shown in FIG. 10. Lambda DNA is 48.5 kb in length, and contains 5 Eco RI sites (Daniels et al, in *Lambda II*, Hendrix et al, Eds. (Cold Spring Harbor, N.Y. 1983), pp. 519–678). The site located at nucleotide position 31,747 was selected for cleavage in order to cut lambda into two fragments of 31.7 and 16.8 kb. An oligonucleotide 30 bases long and homologous to this position was synthesized, and FIG. 10B shows the results of the cleavage using this oligonucleotide. Lane 1 shows uncut lambda DNA, and lane 2 shows a complete cleavage experiment. Densitometry of lane 2 showed that 79% of the DNA was cleaved into the desired two fragments, and 19% of the DNA was uncut. A total of 2% of the DNA was cut at one of the four other Eco RI sites present in lambda DNA, caused by either nonspecific methylation protection by the recA protein and oligonucleotide complex, or incomplete methylation. Controls in lanes 3, 4, and 5 show the result of omitting recA protein, oligonucleotide, or methylase, respectively. Notably, in lane 3, omitting the recA protein resulted in incomplete methylation, possibly due to inhibition of the methylase by free oligonucleotide not coated with recA protein. Lane 4 DNA also showed slightly incomplete methylation, possibly because some nonspecific protection occurred from free recA protein binding to the duplex lambda DNA. This effect was seen more dramatically in FIGS. 11 and 12 where an oligonucleotide titration was done.

EXAMPLE 9

Sequence Specific Cleavage of *E. coli* DNA
Experimental details:

Wild type *E. coli* strain W3110 was obtained from the American Type Culture Collection and was grown overnight in Luria-Bertani medium to an optical density (OD) at 600 nm of 5. 5 ml of cells were pelleted (30 mg wet weight), washed once with 10 mM Tris-HCl (pH 7.2), 20 mM NaCl, and 100 mM EDTA, and resuspended in 1 ml of this buffer. The suspension was brought to 65° C., and added to 1 ml of 1.6% low melting point agarose (InCert agarose, FMC Bioproducts) and 4 ml of paraffin oil at 65° C. Microbeads 25 to 100 µm in diameter were formed by vortexing the suspension as described (M. McClelland, *Methods Enzymol.* 155, 22 (1987)). Beads were digested with lysozyme and proteinase K using the ImBed kit (New England Biolabs) following the manufacturer's directions. Other lysozyme and proteinase K preparations gave equally good results. Beads were stored at 4° C. and were incubated at 50 mM EDTA for 30 minutes and equilibrated in 25 mM Tris-acetate (pH 7.5), 4 mM Mg-acetate, 0.4 mM dithiothreitol, and 0.5 mM spermidine immediately prior to use.

Figure 11A:
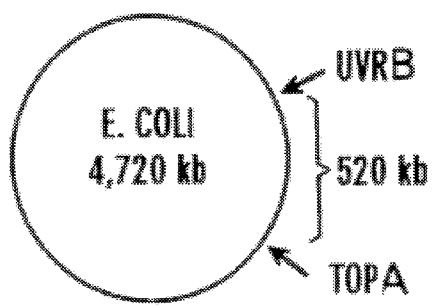
FIG. 11.
FIG. 11B. Agarose gel stained with ethidium bromide showing sequence-specific cleavage of *E. coli* DNA generating a 520 kb fragment. The compression (C) zone of the gel is also shown. Lane Y, yeast *S. cerevisiae* chromosomal DNA markers. Lane lambda, lambda concatamer DNA ladder. Lane E, unmodified *E. coli* DNA after a complete digestion by Eco RI. Lanes 1-5, complete cleavage reactions with different amounts of oligonucleotide in each lane. The uvrB oligonucleotide sequence was 5'-TCATGAGTAAACCGT-TCAAACTGAATTCCGCTTTTA-3' (SEQ ID NO:3) (36 bases long), and the topA sequence was 5'-CGAGATCGAA-GAGGGCGAATTCCGCATTAA-3' (SEQ ID NO:4) (30 bases long). Reaction conditions were similar to those of FIG. 10, except the following conditions were modified to obtain good results for agarose-embedded DNA. RecA protein and oligonucleotide were preincubated with the DNA for 15 minutes at 37° C.; methylase and S-adenosylmethionine were added and the methylation was allowed to proceed for 1 hour. The methylation was terminated by adding 100 µl of 2% SDS for 30 minutes at 37° C. The beads were then equilibrated in 100 mM Tris-HCl (pH 8.0), 50 mM NaCl, 1.5 µM dithiothreitol, and 200 µg/ml nonacetylated BSA (Calbiochem-Behring). The observation of Wilson and Hoffman (Wilson et al, *Anal. Biochem.* 191, 370 (1990)), that this buffer is excellent for inhibiting nonspecific or star activity of Eco RI on agarose-embedded DNA, was confirmed. Concentrations of other reagents are as in FIG. 10 except that each tube contained 20 µg recA protein, the indicated amount of each oligonucleotide, 30 µl (packed volume) of beads containing E. coli DNA, 40 units of methylase, and digestion was with 40 units of Eco RI restriction enzyme. After stopping the reaction, the beads were run on a 1% agarose gel for 30 hours at 12° C., 160 V, with the switch time ranged from 60–140 s.
FIG. 11C. Southern blot of the gel in part (B). The gel was blotted onto a GeneScreen Plus nylon membrane (Dupont) according to the manufacturer's directions. The probe was made by polymerase-chain-reaction amplification (PCR) of a 600 base pair fragment of the trpA gene from E. coli using $^{32}$P-deoxycytidine 5'-triphosphate. The trpA gene lies between the uvrB and the topA gene. The film was overexposed to reveal minor bands, but densitometry was performed on less exposed films. Lane E, which contained the same amount of DNA as lanes 1-5, showed the hybridization of the probe to the predicted 40 kb fragment generated by complete Eco RI digestion (Kohara et al, *Cell* 50, 495 (1987)); the intensity of this band provided the 100% value to calculate the 520 kb fragment yield.
Figure 11B:
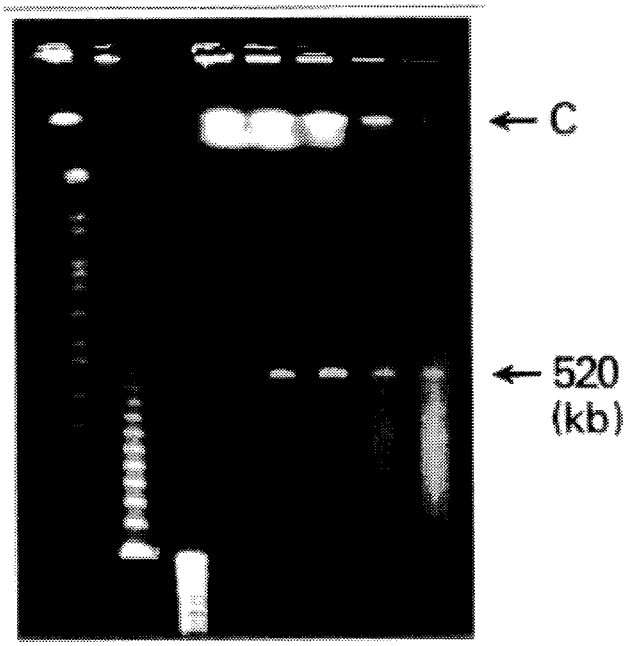
Figure 11C:
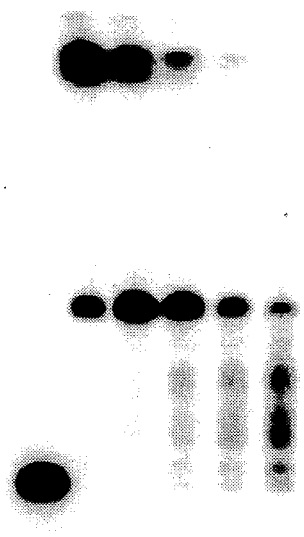

Results:

Application of the cleavage reaction to *E. coli* DNA is shown in FIG. 11. In this case, a pair of oligonucleotides was added to obtain a fragment by cleavage at two sites. A large fragment was generated to test the power of the method. As shown in FIG. 11A, one oligonucleotide was homologous to the uvrB gene, and the other to the topA gene. The oligonucleotides spanned Eco RI sites in each of these genes. The two genes are located 520 kb apart on the chromosome (Rudd et al, *Nucl. Acids Res.* 18, 313 (1990)), and at least 67 Eco RI sites are between these two target sequences (Kohara et al, *Cell* 50, 495 (1987)). FIG. 11B shows the expected 520 kb band. A fairly sharp optimum was observed for oligonucleotide concentration of 5 nucleotide residues per recA protein monomer (lane 2). This was more clearly seen in the Southern blot in FIG. 11C. Densitometry of the blot gave a yield of the fragment of 40%. As in the cleavage of lambda DNA, there was some non-specific protection from methylation by recA protein at lower oligonucleotide concentrations, and the 520 kb fragment was cleaved into smaller fragments. At higher oligonucleotide concentrations, the 520 kb fragment was also cleaved into smaller fragments, as would be expected from the result with lambda DNA in lane 3 of FIG. 10B. An identical pattern with an optimum of 5 nucleotide residues per recA protein monomer was seen when the length of the oligonucleotides was increased from 30 to 60 bases, only in this case the yield of the 20 kb fragment increased to 60%. The 40 and 60% yields for the different pairs of oligonucleotides correspond to minimum single-side cutting efficiencies of 63 and 77%, respectively. This is close to the cutting efficiency on lambda DNA of 79%.

In certain applications, sequence information on both sides of an Eco RI site might be difficult to obtain. The fragment yield was therefore measured when the Eco RI recognition sequence, GAATTC, was at the 5' or the 3' end of a pair of oligonucleotides, instead of in the middle as in the previous study. When the recognition sequence was at the 5' end of the oligonucleotides (30 bases in length), the yield dropped two- to fourfold. When the sequence was at the 3' end, the yield dropped an additional twofold.

EXAMPLE 10

Sequence Specific Cleavage of Human DNA

Experimental Details:

Beads containing HeLa cell DNA were prepared by washing $1\times10^8$ cells (150 mg wet weight) twice with phosphate buffered isotonic saline and processed as in Example 9 for the *E. coli* beads, except that the lysozyme digestion step was omitted.

Figure 12A:
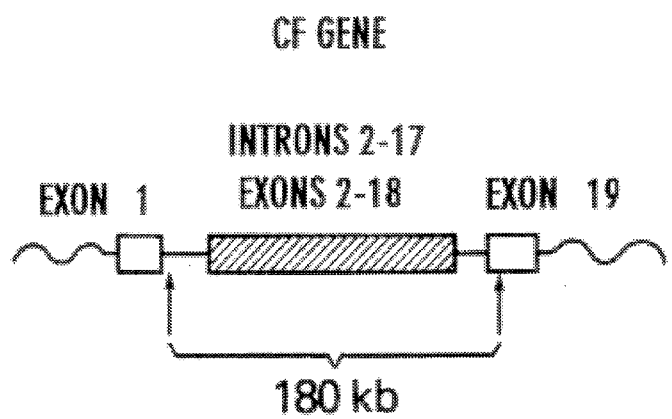
FIG. 12A. A schematic showing the positions of cleavage of the human CF locus using two oligonucleotides homologous to sites in intron 1 and exon 19. The gene contains a total of 24 exons.
Figure 12B:
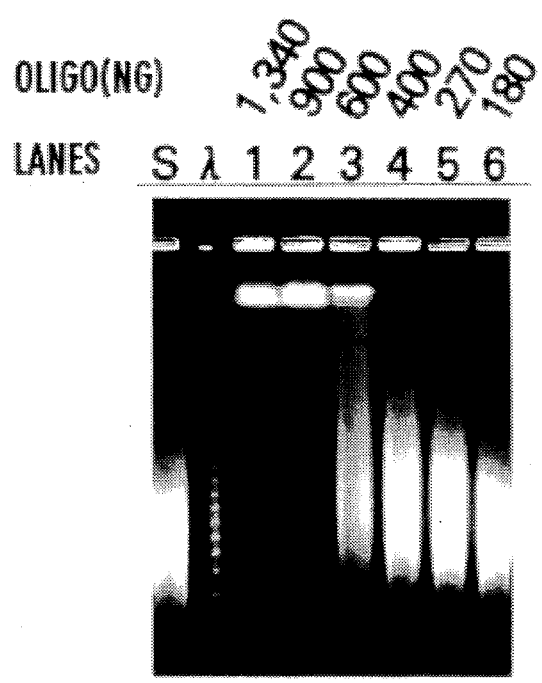
FIG. 12B. Agarose gel stained with ethidium bromide showing development of smaller fragments of DNA as the oligonucleotide concentration was decreased. Lane S, Sfi I digest of unmodified HeLa cell DNA. Lane lambda, lambda concatamer DNA ladder. Lanes 1-6, complete cleavage reactions with the indicated amount of each oligonucleotide. The intron 1 oligonucleotide sequence was 5'-TAAGTGCTCAGAAAACATTTCT-TGACTGAATTCAGCCAA-CAAAAATTTTGGGGTAGGTAG-3' (SEQ ID NO:5) (60 bases long), and the exon 19 oligonucleotide sequence was 5'-AATGGCCAACTCTCGAAAGTTATGAT-TATTGAGAATTCACACGTGAAGA AAGATGA-CATCTGG-3' (SEQ ID NO:6) (63 bases long). Conditions were identical to FIG. 11 except that the reaction volume at all steps was doubled, and 25 µl (packed volume) of HeLa beads were used per reaction. 80 units of Sfi I (New England Biolabs) were used in lane S according to the manufacturer's directions. A 1% agarose gel was run for 32 hours at 12° C., 160 V, with the switch time ramped from 40–120 s.
Figure 12C:
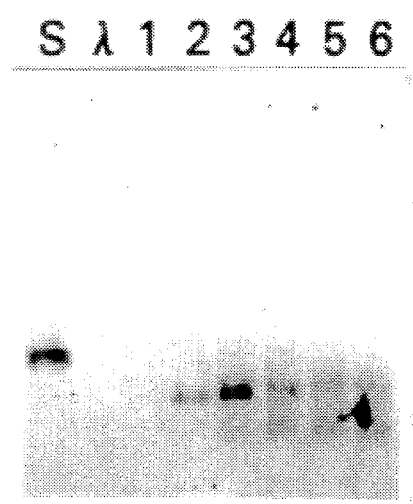
FIG. 12C. Southern blot of the gel in part (B). The Sfi I digest band was 270 kb long and was used in calculating the yield of the 180 kb fragment. The probe was made by PCR of the CF cDNA T8-B3 plasmid (from the American Type Culture Collection). The probe was 550 bases long and contained 410 bases of exon 13 colinear with 140 bases of exon 14.

Results:

The cleavage reaction was performed on human DNA with similar success. As the cystic fibrosis (CF) locus has been extensively mapped and sequenced (Rommons et al, *Science 245, 1059* (1989); Riordan et al, *Science* 245, 1066 (1989); Zielenski et al, *Genomics* 10, 214 (1991)), it was used as a locus to test the method. FIG. 12A is a simple schematic of the CF locus. An Eco RI site is present in intron 1, and is 180 kb away from another Eco RI site in exon 19. At least 41 other Eco RI sites are found on this 180 kb stretch of genomic DNA (Rommons et al, *Science* 245, 1059 (1989)). A gel stained with ethidium bromide is shown in FIG. 12B, and shows how the production of smaller fragments occurred when the oligonucleotide concentration was lowered. This pattern was very reproducible and could be used as a guide to find the optimal concentration of oligonucleotide without doing Southern blotting. The Southern blot of the gel is shown in FIG. 12C. The greatest yield of the fragment was found in lane 3 (86%). A smaller yield (32%) was found in lane 2, but the background cleavage in lane 2 was much lower than in lane 3. Thus, DNA from the 180 kb region of lane 2 probably was the most enriched in DNA from the CF locus. A control shown in lane S is the 270 kb fragment produced by digestion with Sfi I (Rommons et al, *Science* 245, 1059 (1989)). A predicted 48 kb fragment could also be produced by specific cleavage at exons 13 and 19.

It was also noted in FIG. 12C that in lanes 3–6, the 180 kb fragment was further broken down to smaller fragments. These fragments were probably generated by one specific cleavage at intron 1 or exon 19, and one nonspecific cleavage of the fragment internally. As the probe used is 50 kb from the exon 19 site, no fragments under 50 kb in length hybridized, although presumably they were present.

The entire contents of all references cited above are incorporated herein by reference.

Certain aspects of the present invention have been described in some detail for purposes of clarity and understanding. One skilled in the art will appreciate, however, that various changes can be made in form and detail without departing from the true scope of the invention.

What is claimed is:

1. A method of selecting for a specific double-stranded DNA molecule present in a sample comprising:
   i) contacting a recombination protein with said double-stranded DNA molecule and with a single-stranded DNA molecule, which single-stranded DNA molecule is sufficiently complementary to a specific sequence present in said double-stranded DNA molecule to hybridize therewith, wherein said contacting is effected in the presence of ADP and ATP-gamma-S and under conditions such that said single-stranded DNA molecule hybridizes to said double-stranded molecule so that a three-stranded DNA molecule is formed, wherein said single-stranded DNA molecule has a first member of a binding pair bound thereto;
   ii) separating said three-stranded DNA molecule from unhybridized single-stranded DNA molecules;
   iii) contacting said three-stranded DNA molecule with a second member of said binding pair; and
   iv) isolating said three-stranded DNA molecule bound to said second member of said binding pair.

2. The method according to claim 1 wherein ATP-gamma-S and ADP are present during said contacting of step (i) in a molar ratio of about 1:3.

3. The method according to claim 1 wherein ADP is present during said contacting of step (i) at a concentration of about 1.1 mM.

4. The method according to claim 1 wherein ATP-gamma-S is present during said contacting of step (i) at a concentration of about 0.3 mM.

5. The method according to claim 1 wherein said contacting of step (i) is effected in the presence of magnesium and spermidine.

6. A method of effecting cleavage of a double-stranded

DNA molecule containing at least two restriction endonuclease recognition sites at a first of said sites by a restriction enzyme specific for said sites comprising:

i) contacting a recombination protein with the double-stranded DNA molecule and with a single-stranded DNA molecule, which single-stranded DNA molecule is sufficiently complementary to a portion of one strand of said double-stranded DNA molecule that includes the first of said restriction endonuclease recognition sites to hybridize therewith, wherein said contacting is effected under conditions such that said single-stranded DNA molecule hybridizes to said double-stranded molecule at said first of said restriction endonuclease recognition sites so that a three-stranded DNA molecule is formed, and ii) methylating the at least one other of said sites so as to render it protected from said restriction enzyme;

iii) dissociating said single-stranded DNA molecule from said double stranded molecule; and iv) cleaving said double-stranded molecule resulting from step (iii) at said first of said restriction sites.

7. A method of protecting a sequence of a double-stranded DNA molecule from modification by a methylase comprising:

i) contacting a recombination protein with the double-stranded DNA molecule and with a single-stranded DNA molecule, which single-stranded DNA molecule is sufficiently complementary said sequence of said double-stranded DNA molecule to hybridize therewith, wherein said contacting is effected under conditions such that said single-stranded DNA molecule hybridizes to said sequence of said double-stranded molecule so that a three-stranded DNA molecule is formed, and ii) contacting said three-stranded DNA molecule with said methylase under conditions such that said three-stranded DNA molecule remains intact, whereby said sequence is protected from modification.

8. The method according to claim 6 or 7 wherein said contacting of step (i) is effected in the presence of ATP-gamma-S and ADP.

9. The method according to claim 8 wherein ATP-gamma-S and ADP are present during said contacting of step (i) in a molar ratio of about 1:3.

10. The method according to claim 8 wherein ADP is present during said contacting of step (i) at a concentration of about 1.1 mM.

11. The method according to claim 8 wherein ATP-gamma-S is present during said contacting of step (i) at a concentration of about 0.3 mM.

12. The method according to claim 8 wherein said contacting of step (i) is effected in the presence of magnesium.

13. The method according to claim 12 wherein the concentration of magnesium is at least 4 mM.

14. The method according to claim 12 wherein said contacting of step (i) is effected in the presence of spermidine.

15. A method of inhibiting transcription or replication of a specific sequence present on one strand of a double-stranded DNA molecule comprising contacting a recombination protein with said double-stranded DNA molecule and with a single-stranded DNA molecule, which single-stranded DNA molecule is sufficiently complementary to said sequence to hybridize therewith, wherein said contacting is effected under conditions such that said single-stranded DNA molecule hybridizes to said gene sequence so that a three-stranded DNA molecule is formed, whereby transcription and replication of said sequence is inhibited.

16. A method of protecting a double-stranded DNA molecule containing at least two restriction endonuclease recognition sites from cleavage by a restriction endonuclease at a first of said restriction endonuclease recognition sites comprising:

i) contacting a recombination protein with the double-stranded DNA molecule and with a single-stranded DNA molecule, which single-stranded DNA molecule is sufficiently complementary to a portion of one strand of said double-stranded DNA molecule that includes said first restriction endonuclease recognition site to hybridize therewith, wherein said contacting is effected in the presence of ATP-gamma-S and ADP and under conditions such that said single-stranded DNA molecule hybridizes to said double-stranded molecule at said first restriction endonuclease recognition site so that a three-stranded DNA molecule is formed; and ii) contacting said three-stranded DNA molecule with said restriction endonuclease under conditions such that said three-stranded DNA molecule remains intact, whereby said first restriction endonuclease recognition site is protected from cleavage.

17. The method according to claim 16 wherein said contacting of step (i) is effected in the presence of spermidine and magnesium.

18. The method according to claim 16 wherein, during the contacting of step (i), ATP-gamma-S and ADP are present in a molar ratio of about 1:3.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 30 base pairs (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

TATCAACCGG GGTACATATG ATTGACATGC                                           30

(2) INFORMATION FOR SEQ ID NO:2:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

TCACGCCGGA AGTGAATTCA AACAGGGTTC                                           30

(2) INFORMATION FOR SEQ ID NO:3:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

TCATGAGTAA ACCGTTCAAA CTGAATTCCG CTTTTA                                    36

(2) INFORMATION FOR SEQ ID NO:4:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

( v i ) ORIGINAL SOURCE:

( x i ) SEQUENCE DESCRIPTION: SEQ ID NO:4:

CGAGATCGAA GAGGGCGAAT TCCGCATTAA 30

( 2 ) INFORMATION FOR SEQ ID NO:5:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

TAAGTGCTCA GAAAACATTT CTTGACTGAA TTCAGCCAAC AAAAATTTTG GGGTAGGTAG 60

( 2 ) INFORMATION FOR SEQ ID NO:6:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

AATGGCCAAC TCTCGAAAGT TATGATTATT GAGAATTCAC ACGTGAAGAA AGATGACATC 60

TGG 63

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

TTGACAGCTT ATCATCGATA 20

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:8:

GAATATATGC ATCATCGATA                    20

( 2 ) INFORMATION FOR SEQ ID NO:9:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:9:

GAATATATGC CACATCGATA                    20

( 2 ) INFORMATION FOR SEQ ID NO:10:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:10:

GAATATATGC CATGTCGATA                    20

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

GAATATATGC CATGGAGATA 20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

GAATATATGC CATGGATCGT 20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

ATCATCGATA AGCTTTAATG 20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

ATCATCGATA GAATATATGC 20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:15:

ATCATCGAGC GAATATATGC        20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:16:

ATCATCTCGC GAATATATGC        20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:17:

ATCAGATCGC GAATATATGC        20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:18:

CGACGATCGC GAATATATGC    20

(2) INFORMATION FOR SEQ ID NO:19:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:19:

AAGCTTGCAT GCCTGCAGGT CGACTCTAGA GGATCCCCGG GTACCGAGCT CGAATTC    57

(2) INFORMATION FOR SEQ ID NO:20:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:20:

TCGAACGTAC GGACGTCCAG CTGAGATCTC CTAGGGGCCC ATGGCTCGAG CTTAAG    56

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:21:

GCCCCTAGGA GATCTCAGCT    20

( 2 ) INFORMATION FOR SEQ ID NO:22:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:22:

GAATTCGAGC TCGGTACCCG GGGATCCTCT AGAGTCGACC TGCAGGCATG CAAGCTT     57

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:23:

ACTGCGTAAC GGTAGCATGA     20

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:24:

ACCGATCTGA CGTGAGTGAC     20

( 2 ) INFORMATION FOR SEQ ID NO:25:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:25:

ACTGCGTAAC GGTAGCATGA ACCGATCTGA CGTGAGTGAC 40

( 2 ) INFORMATION FOR SEQ ID NO:26:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:26:

AGCTTATCAT CGATA 15

( 2 ) INFORMATION FOR SEQ ID NO:27:

( i ) SEQUENCE CHARACTERISTICS:
( A ) LENGTH: 15 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:27:

AGCTTATCAT CGATA 15